United States Patent
Sivarasu et al.

(10) Patent No.: US 11,213,636 B2
(45) Date of Patent: Jan. 4, 2022

(54) ASSISTIVE DEVICE FOR AN INHALER

(71) Applicant: University of Cape Town, Cape Town (ZA)

(72) Inventors: Sudesh Sivarasu, Cape Town (ZA); Giancarlo Lanfranci Beukes, Cape Town (ZA); Jason Dirk Voorneveld, Rotterdam (NL); Michael Levin, Cape Town (ZA)

(73) Assignee: University of Cape Town, Cape Town (ZA)

( * ) Notice: Subject to any disclaimer, the term of this patent is extended or adjusted under 35 U.S.C. 154(b) by 638 days.

(21) Appl. No.: 16/087,362

(22) PCT Filed: Mar. 14, 2017

(86) PCT No.: PCT/IB2017/051462
§ 371 (c)(1),
(2) Date: Sep. 21, 2018

(87) PCT Pub. No.: WO2017/163147
PCT Pub. Date: Sep. 28, 2017

(65) Prior Publication Data
US 2021/0205551 A1    Jul. 8, 2021

(30) Foreign Application Priority Data
Mar. 21, 2016  (GB) ..................... 1604709

(51) Int. Cl.
*A61M 15/00*  (2006.01)
(52) U.S. Cl.
CPC ...... *A61M 15/0075* (2014.02); *A61M 15/009* (2013.01); *A61M 2205/586* (2013.01); *A61M 2205/59* (2013.01)

(58) Field of Classification Search
CPC ............ A61M 15/0075; A61M 15/009; A61M 2205/586; A61M 2205/59
See application file for complete search history.

(56) References Cited

U.S. PATENT DOCUMENTS

| 5,899,365 A | * | 5/1999 | Eichler | ............. A61M 15/0001 |
| | | | | 222/162 |
| 2001/0013343 A1 | * | 8/2001 | Andersson | .......... A61M 15/009 |
| | | | | 128/200.24 |

(Continued)

FOREIGN PATENT DOCUMENTS

| EP | 1066075 A1 | 1/2001 |
| WO | WO-96/11152 A1 | 4/1996 |

(Continued)

OTHER PUBLICATIONS

Combined Search and Examination Report under Sections 17 and 18(3) for Application No. GB1604709.4, dated Aug. 18, 2016 (5 pages).

(Continued)

*Primary Examiner* — Steven O Douglas
(74) *Attorney, Agent, or Firm* — Clark & Elbing LLP

(57) ABSTRACT

An assistive device for a metered dose inhaler decreases the force required to operate the inhaler. The assistive device has a body with a passage for receiving a replaceable conventional metered dose inhaler assembly that has a canister and a transverse mouthpiece with an axis of the canister aligning approximately with that of the passage. At least two symmetrically arranged levers extend in a direction away from the body and parallel to an axis thereof. A proximal end of each lever is attached to the body such that the free opposite ends of the levers may be moved towards and away from each other. An inwardly directed cam surface on each of the levers engages a closed end of a canister in use to move the (Continued)

canister longitudinally to cause a dose of medicament to be dispensed from the canister. An optional dose counter may form part of the device.

14 Claims, 4 Drawing Sheets

(56) References Cited

U.S. PATENT DOCUMENTS

| | | |
|---|---|---|
| 2003/0084899 A1 | 5/2003 | Andersson |
| 2004/0245291 A1 | 12/2004 | Simon et al. |
| 2005/0194006 A1 | 9/2005 | Hoang |
| 2008/0168984 A1 | 7/2008 | Lintern et al. |
| 2008/0190419 A1 | 8/2008 | Pearson et al. |
| 2009/0229604 A1 | 9/2009 | Pearson et al. |
| 2013/0139814 A1 | 6/2013 | Mullane et al. |
| 2014/0318534 A1* | 10/2014 | Engelbreth ............ A61M 11/08 128/200.23 |
| 2016/0129206 A1 | 5/2016 | Engelbreth |

FOREIGN PATENT DOCUMENTS

| | | |
|---|---|---|
| WO | WO-2006/097728 A1 | 9/2006 |
| WO | WO-2006/097745 A1 | 9/2006 |
| WO | WO-2006/097756 A1 | 9/2006 |
| WO | WO-2007/028992 A1 | 3/2007 |
| WO | WO-2008/110584 A2 | 9/2008 |
| WO | WO-2014/140724 A1 | 9/2014 |

OTHER PUBLICATIONS

International Search Report for International Patent Application No. PCT/IB2017/051462, dated Sep. 20, 2017 (6 pages).

Written Opinion of the International Searching Authority for International Patent Application No. PCT/IB2017/051462, dated Sep. 20, 2017 (8 pages).

* cited by examiner

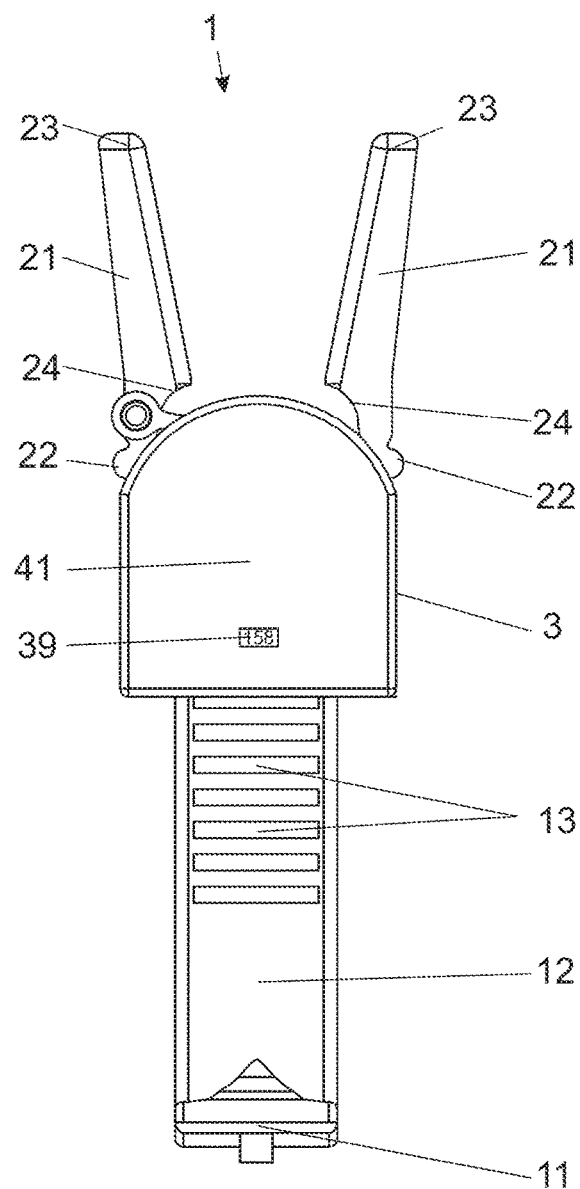
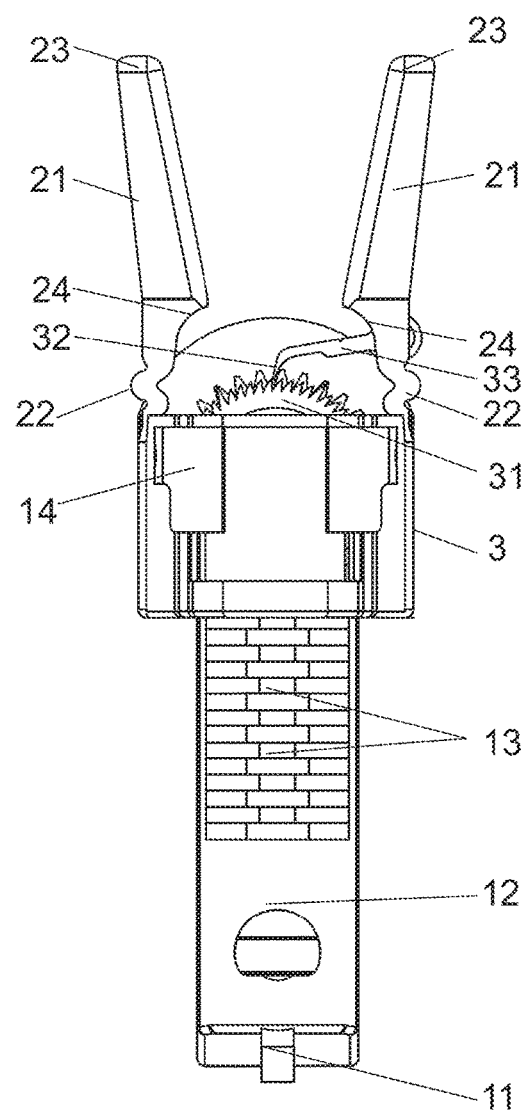
Figure 3
Figure 4

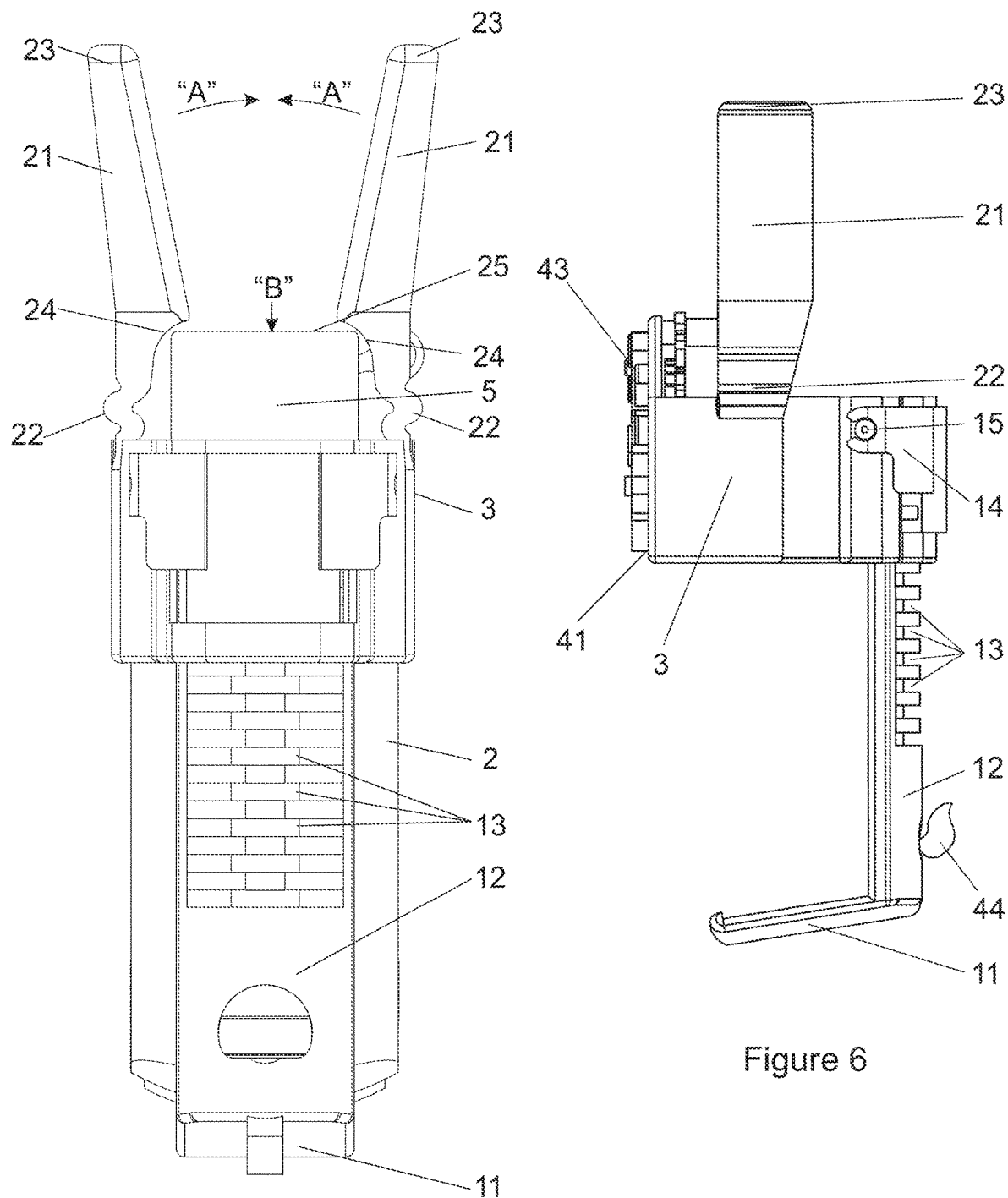

ASSISTIVE DEVICE FOR AN INHALER

CROSS-REFERENCE(S) TO RELATED APPLICATIONS

This application claims priority from United Kingdom patent application number 1604709.4 filed on Mar. 21, 2016, which is incorporated by reference herein.

FIELD OF THE INVENTION

This invention relates to an assistive device for an inhaler whereby medication can be administered to a patient for delivering medication to the body via the respiratory system and, more particularly, to an assistive device that can be configured to effectively reduce the force necessary to administer medication from an inhaler. Such an assistive device it is envisaged would be particularly useful to pediatric and geriatric patients that may have difficulty in applying sufficient force to an inhaler to release the medication.

In particular, but not exclusively, the invention relates to an assistive device for metered dose inhaler that is a rather common form of inhaler currently available.

BACKGROUND TO THE INVENTION

An inhaler is a handheld aerosol device that uses a propellant to deliver a therapeutic agent. An inhaler typically includes a pressurized metal canister that contains the pharmacological agent in suspension or solution, a surfactant, and a propellant with the metal canister being fitted with a discharge valve that in the case of a metered dose inhaler takes the form of a metering valve. The canister is generally housed in a plastic sleeve that has a mouthpiece for drug delivery. Actuation or triggering of the canister produces a fine atomized spray that delivers a dose. In the case of a metered dose inhaler the delivery typically takes place over a time period of about 100-200 milliseconds which varies according to the particular medication and application.

To actuate the conventional manually operable inhaler, the user applies an axially directed compressive force to the closed end of the canister. The internal components of the discharge of metering valve assembly are spring loaded so that a compressive force reportedly of about 15 to 30 N, and sometimes more, is required to activate the device. In response to this compressive force, the canister moves axially with respect to the valve stem by an amount varying from about 2 to about 4 mm which is sufficient to actuate the discharge or metering valve and cause a quantity of the drug and propellant to be expelled through a valve stem. A user inhaling through the drug delivery outlet of the inhaler device at this point thereby receives a dose of the drug.

The force needed to administer a dose is considerable to some patients of lesser physical ability, in particular children and geriatrics. Such persons are sometimes unable to exert the required force or at least have considerable difficulty in doing so. In order to combat this, more sophisticated inhaler devices have been proposed and are available commercially, but these are not affordable to many of lesser means. Some sophisticated devices even use the patient's breath to activate them but they are considerably more costly than a simple inhaler device.

For example, United States publication US2003084899 describes an inhalation device in which diametrically opposite actuating members are hingedly attached to sidewalls of a body member with the point of physical application of force to the actuating members being between the hinged attachment to the sidewalls of the body and inclined inwardly facing surfaces that engage diametrically opposite bottom corners of an inverted canister and cause the dispensing of a dose of medicament. The result is a third order lever system in which the resistance (or load) is on one side of the point at which physical effort is applied to the actuating members and the fulcrum is located on the other side of the point of application of the physical effort. The mechanical advantage of such a third order lever system is always less than 1 and it therefore does not assist the user from a physical perspective. Also, with this physical arrangement the range of movement of the actuating members is limited by the presence of the canister in between them. Accordingly, a desired mechanical advantage cannot be achieved in any way with this arrangement.

There is a need for an assistive device that can be used in combination with a conventional inhaler in order to decrease the force required to activate the inhaler.

Conventional metered dose inhalers containing multiple doses typically contain in the range of 100 to 300 and quite commonly about 200 doses. As the canisters are not transparent, a record needs to be made of how many doses have been taken and therefore how many doses remain in the canister. Considerable inventive activity has been exerted towards the creation of effective dose counters some of which are electronic in nature and others of which are purely mechanical. The latter may operate on the basis of a pawl that is movable longitudinally and rotates a toothed wheel one tooth at a time as part of a dose tracking technology. Unfortunately, most of these dose counters are also costly and are not affordable by those of lesser means.

There is therefore also a need for an assistive device that embodies a simple and inexpensive dose counter.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided an assistive device for an inhaler wherein the assistive device comprises a body defining a passage configured to receive a conventional inhaler assembly including a canister and transverse mouthpiece with an axis of the canister of the inhaler assembly approximately aligning with an axis of the passage through the body of the assistive device, a foot associated with the body for supporting a mouthpiece of the inhaler assembly at one end of the body when such an inhaler assembly is installed therein, and at least two symmetrically arranged levers supported by the body adjacent the passage and extending in a direction away from the foot and generally parallel to an axis of the body with a proximal end of each of the levers being attached to the body by an attachment that enables free opposite ends of the levers to be moved towards and away from each other, and an inwardly directed cam surface on each of the levers that is configured to engage a closed end of a canister of a conventional inhaler assembly when it is installed in the assistive device to move the canister longitudinally towards the foot and cause medicament to be dispensed from the canister.

Further features of the invention provide for the foot to be carried by a leg extending from the body; for the length of the leg to be telescopically adjustable to accommodate different lengths of conventional inhaler assemblies; for the leg to have a series of formations along a part of its length that may be selectively engaged by a releasable locking member that in its operative position is axially stationary relative to the body in order to set an adjustable position of the foot relative to the body; for there to be either two or three levers symmetrically arranged relative to the passage with the cam surfaces thereof projecting into the line of the passage so as to cooperate with corners of a closed end of a canister of a conventional inhaler when it is installed in the assistive device with its closed end located on the outside of the body on the side thereof opposite the foot; for the cam surfaces to be curved inwardly and to be designed to achieve a suitable longitudinal movement of a canister during movement of the levers towards each other so that a dose of medication can be delivered by operation of the levers; and for the cross-sectional size of the passage through the body to be adjustable to accommodate different diameters of inhalers; and for the conventional inhaler to be a metered dose inhaler.

Further features of the invention provide for the assistive device to be especially configured for use with a metered dose inhaler and the body of the assistive device has a support on one side thereof that supports a toothed gear dose counting mechanism having the axes of the gears extending at generally right angles to the axis of the passage with one of the toothed gears co-operating with a pawl carried on one end of a transverse arm that has its other end pivotally attached to one of the levers so that it moves transversely relative to the axis of the passage in a reciprocal manner as the levers are moved towards and away from each other; for the pawl driven gear to have radially shorter teeth interposed between radially longer teeth such that only the longer teeth transfer any movement to gears driven by the driven gear; and for the toothed gear mechanism to include a pawl driven gear, a transfer gear, and a display gear carrying numerals that are visible through a suitable aperture to indicate doses remaining or doses already delivered.

It will be understood that the levers in the case of the assistive device according to this invention are in an arrangement complying with that of a second order lever system in which the mechanical advantage is always greater than 1. Furthermore, as the canister is not indeed present between the levers themselves and only between the cam surfaces, the range of movement of the levers towards each other is not restricted by an interposed canister and the design may be such that the levers can move towards each other until they are almost in contact. An appropriate mechanical advantage greater than 1 can therefore be achieved and the design of the levers and cam surfaces can be targeted at achieving a desired mechanical advantage greater than 1.

Whilst both of the two levers or three levers envisaged above may be movable about their proximal ends, it is to be understood that the principles of the invention would also be fulfilled if one lever were fixed relative to the body and, in the case of a two lever arrangement, only the other one would be movable thereby nevertheless rendering the levers movable towards and away from each other.

For pediatric purposes the assistive device could be made to resemble a comic character in which instance the aperture could be a mouth or eye through which the number of remaining or delivered doses can be viewed and an outer cover for the gear mechanism could support a comic face for example. It would be preferred that only two levers be used in such an instance and they could be made to resemble long ears, for example, such as of a rabbit.

In order that the invention may be more fully understood, one embodiment thereof will now be described by way of example only with reference to the accompanying drawings.

BRIEF DESCRIPTION OF THE DRAWINGS

In the drawings:

FIG. 3 is a front view of the assistive device with the metered dose inhaler removed;

FIG. 4 is a rear view of the assistive device with the metered dose inhaler removed;

FIG. 5 is a somewhat enlarged rear view with the metered dose inhaler in place and showing the relationship between the end of the inhaler canister and the levers;

FIG. 6 is a side view of the assistive device with the metered dose inhaler removed;

DETAILED DESCRIPTION WITH REFERENCE TO THE DRAWINGS

Figure 1:
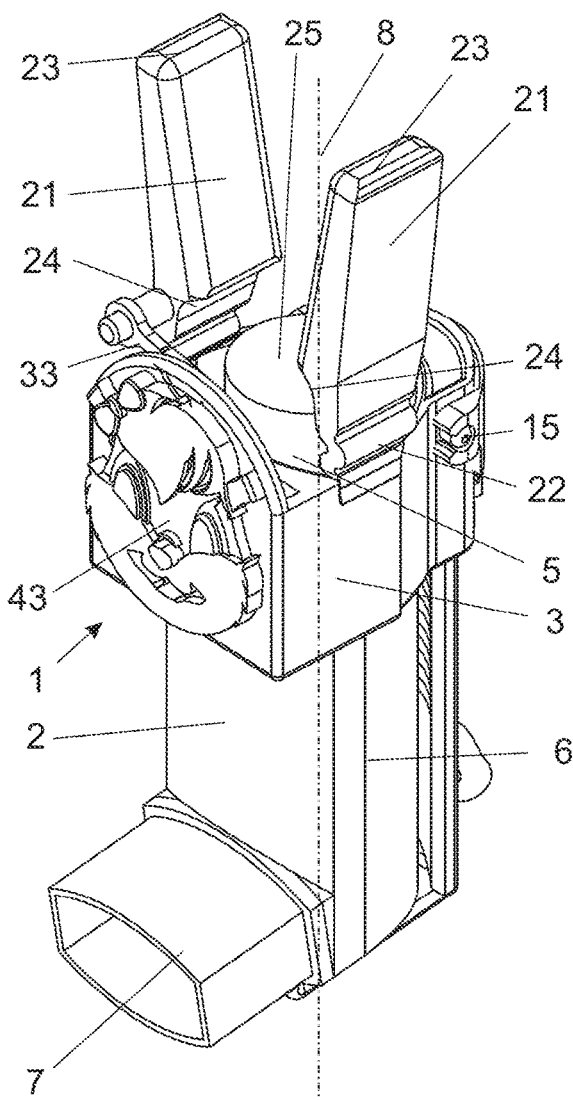
FIG. 1 is a perspective view of one embodiment of assistive device according to the invention showing a conventional metered dose inhaler in position in the device.
Figure 2:
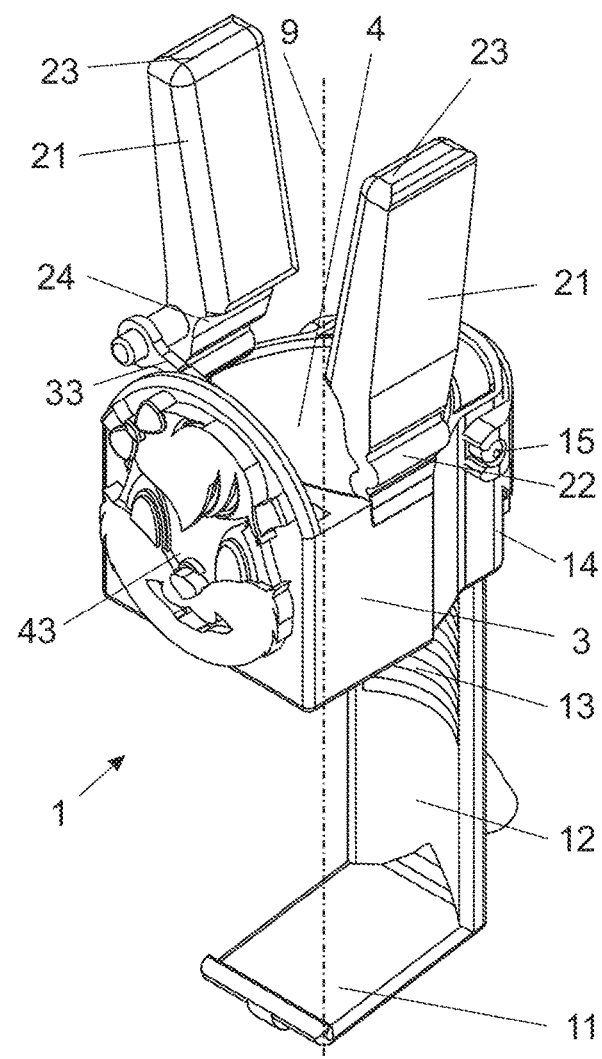
FIG. 2 is a similar view of the same embodiment of the invention with the metered dose inhaler removed.
Figure 7:
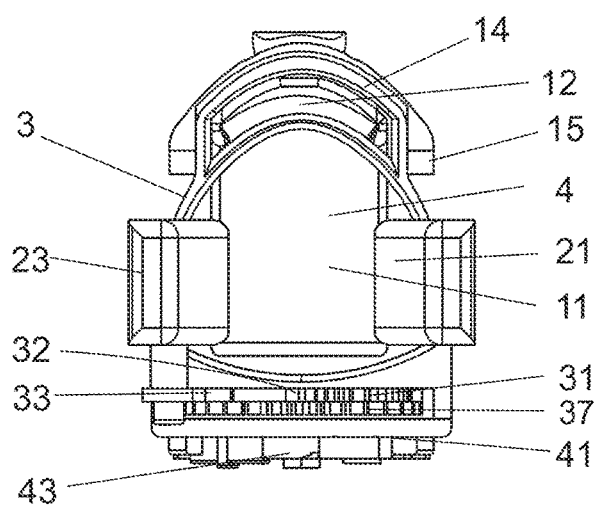
FIG. 7 is a plan view of the assistive device with the metered dose inhaler removed.

In the embodiment of the invention illustrated in the drawings, an assistive device, generally indicated by numeral (1), for a metered dose inhaler (2) comprises a body (3) defining a passage (4) configured to receive a conventional metered dose inhaler assembly. The metered dose inhaler includes a canister (5) fitted with the usual outer sleeve (6) having a transverse mouthpiece (7) with an axis (8) of the canister of the inhaler assembly approximately aligning with an axis (9) of the passage through the body of the assistive device. The inhaler assembly is illustrated in FIGS. 1 and 5. The cross-sectional shape of the passage conforms to the cross-sectional shape of the inhaler that is typically basically a somewhat rounded D-shape.

A foot (11) supports the mouthpiece of the metered dose inhaler assembly at one end of the body when such a metered dose inhaler assembly is installed therein. The foot is carried by a leg (12) extending from the body with the length of the leg being telescopically adjustable relative to the body to accommodate different lengths of conventional metered dose inhaler assemblies. The leg has a series of formations in the form of transverse grooves (13) along a part of its length that may be selectively engaged by a releasable locking member (14) that in its operative position is axially stationary relative to the body. The locking member is rotatable between inoperative and operative positions about pivots (15) formed integral with the body and it has projections corresponding to the grooves with two projections conveniently being engaged with the leg by way of a window through the wall of the body.

Two symmetrically arranged levers (21) are supported by the body adjacent the passage and the levers extend in a direction away from the foot and generally parallel to the axis (9) of the body with a proximal end (22) of each of the levers being attached to the body by an attachment that is optionally integral to create living hinges and is configured to enable free opposite ends (23) of the levers to be moved towards and away from each other in a generally arcuate manner. Of course, the levers may be attached to the body by means of pivots or hinges but that would quite possibly increase the cost of the assistive device somewhat which may or may not be significant.

Each lever has an inwardly directed curved cam surface (24) that is configured to engage a closed end (25) of a canister of a conventional metered dose inhaler assembly when it is installed in the assistive device to move the canister longitudinally towards the foot and cause a dose of medicament to be dispensed from the canister. The relationship between the canister end and the cams on the levers is shown clearly in FIG. 5.

The cam surfaces project partially into the line of the passage so as to be in line with diametrically opposite corners of a circular closed end of a canister of a conventional metered dose inhaler when it is installed in the assistive device with its closed end projecting from the side of the body opposite the foot. The cam surfaces are curved inwardly and are designed to achieve a suitable longitudinal movement of a canister during movement of the levers towards each other to deliver a dose of medicament.

As indicated in FIG. 5, inward arcuate movement of the levers as indicated by arrows "A" is translated by the cam surfaces in to longitudinal movement as indicated by arrow "B" of the canister towards the foot to cause a dose of medicament to be dispensed from the canister. The shape of the cam surfaces can accordingly be varied as may be appropriate or desired so that it achieves these basic objectives when the levers are moved towards each other about their attachments to the body.

The lengths of the levers can be selected according to the mechanical advantage to be achieved coupled with the limitation that the levers should not be too long as that may restrict their arcuate movement and also make them rather cumbersome. However, a certain minimum length would be required in order to achieve the objectives of the invention.

The levers may be resiliently biased to their outer positions independently of the canister or they may be urged to their outer positions by spring loading contained within the metering valve assembly of the metered dose inhaler assembly, or both.

The levers are, as indicated above, in an arrangement that complies with the requirements of a second order lever system in which the mechanical advantage is always greater than 1. As the canister is not present between the levers themselves and only between the cam surfaces, the range of movement of the levers towards each other is not restricted by any interposed canister.

Figure 8:
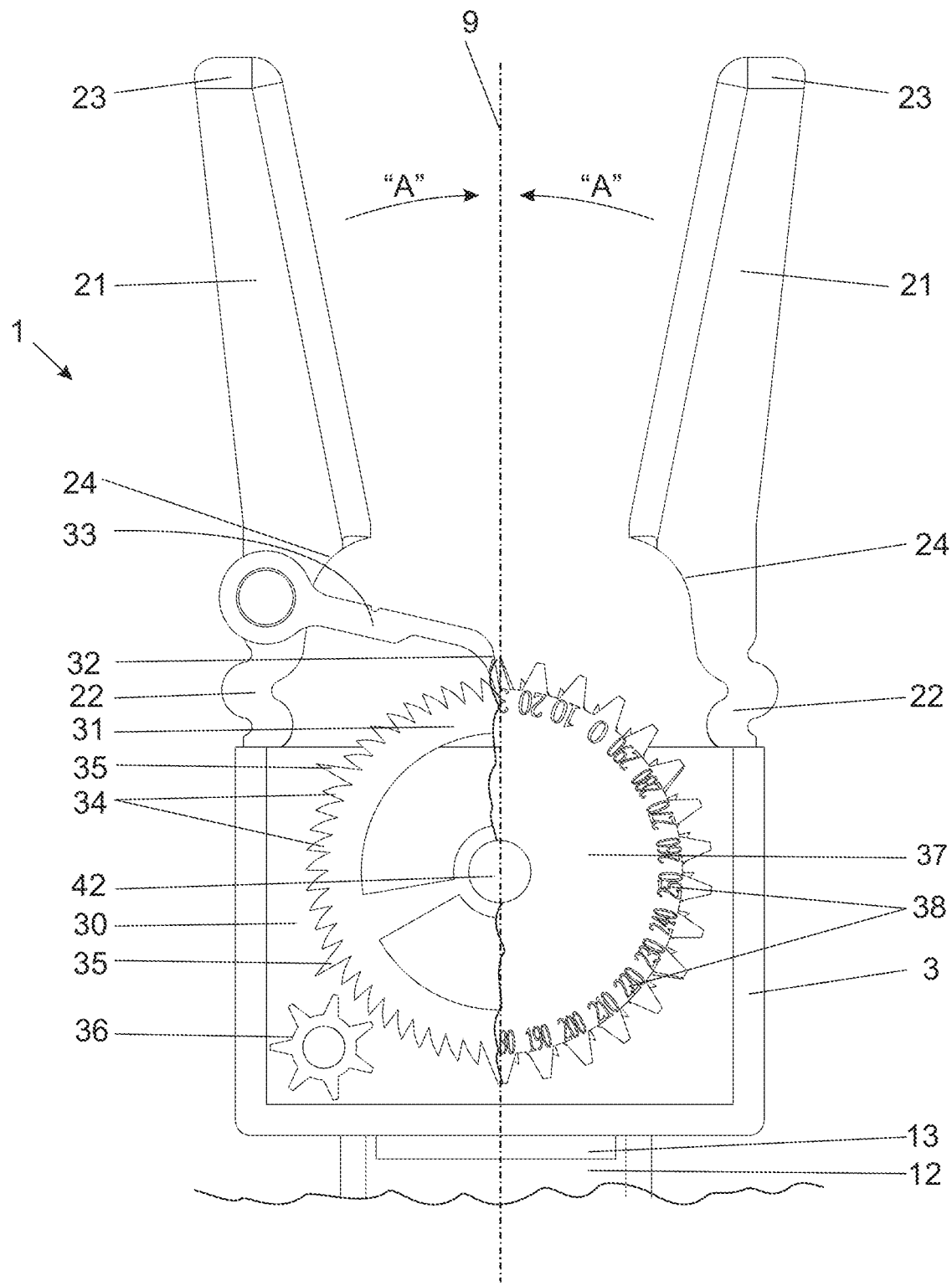
FIG. 8 is an enlarged front view of the body of the device with the front removed and the forward display gear partially broken away to reveal the rear pawl driven gear behind it.

As shown most clearly in FIG. 8, the body has a support in the form of a flat face (30) on one side thereof that supports a toothed gear mechanism having the axes of the gears extending at generally right angles to the direction of the axis of the passage. One of the toothed gears is a pawl driven gear (31) that co-operates with a pawl (32) at one end of a transverse arm (33) pivotally attached at its other end to one of the levers (21) so that it moves transversely relative to the axis of the passage in a reciprocal manner as the levers are moved towards and away from each other. This pawl driven gear has radially shorter teeth (34) interposed between radially longer teeth (35) that constitute, in this particular instance, every tenth gear tooth such that only the longer teeth transfer any movement to a transfer gear (36) that cooperates with both the pawl driven gear and with a display gear (37) mounted coaxially with the pawl driven gear.

The display gear (37) carries numerals (38) that are visible through a suitable aperture (39) (see FIG. 3) in a visible front face (41) of the body to indicate doses remaining or doses already delivered. The display gear is rotatable independently about the same axle (42) as the pawl driven gear so that differential angular movements of these two gears are enabled. The arrangement is such that with a total of say sixty teeth on the pawl driven gear (one in ten being of the longer type and the sixty being selected to ensure that the spacing between the teeth results in the required movement of the arm and pawl to effectively result in the rotation of the pawl driven gear) and thirty teeth on the display gear, one revolution of the display gear will correspond to a total of 300 doses if each tooth is provided with a total number in increments of 10 (often 290 if the first one is labelled "0"). Of course, the display gear can be configured to be set either to "0" or the maximum number of doses that is expected of a particular type of metered dose inhaler assembly at the time that a new metered dose inhaler assembly is installed in the assistive device. The arrangement may thus be such that the numeral displayed in the aperture corresponds to a number of doses already delivered or corresponds to a number of projected doses remaining in the metered dose inhaler assembly.

The visible front face of the body may be used to carry any type of indicia or ornamentation with a plain face being illustrated in FIG. 3 and a relief image cartoon character face (43) being illustrated in FIGS. 1, 2, 6 and 7. In the latter instance the levers can be made to appear as ears of the cartoon character and the leg may be provided with a simulated tail (44) (see FIG. 6) that can also be used as a handle for extending and retracting the leg as may be required.

In use, with a standard metered dose inhaler assembly installed within the assistive device, the levers can be moved towards each other to cause the cams to engage two opposite edges of the closed end of the canister to a move it in a direction towards the foot and mouthpiece supported by it until a dose of medication is delivered.

During this movement the transverse arm and pawl that it carries are moved inwards such that the pawl engages a tooth of the pawl driven gear to rotate it by an amount corresponding to the pitch of the gear teeth. When the arm and pawl return after the force is removed, the pawl moves over an adjacent tooth of the pawl driven gear and into a gap between the next two adjacent teeth ready for the next operation.

It will be understood that the transfer gear is only rotated by one gear tooth for every 10 doses administered by the metered dose inhaler assembly that in turn rotates the display gear by one tooth. A numeral reflecting either how many doses have been delivered by the metered dose inhaler or how many are remaining in the metered dose inhaler will be visible through the aperture (39).

The length of the leg and therefore the position of the foot can be easily adjusted by disengaging the locking member from the grooves in the leg and adjusting the position of the leg telescopically relative to the body of the assistive device. The assistive device can thus be used in combination with a number of different metered dose inhalers.

In trials conducted to date, the amount of force required to activate a standard inhaler without the assistive device of this invention was measured to be 39.23N. The amount of force required to activate the same inhaler with the assistive device of the invention was 12.26N which is a substantial improvement at relatively little additional cost when taking into account that the assistive device is reusable and does not have to be discarded with the inhaler. It should be noted that the force required to activate the inhaler described in US2003084899 would be greater than the 39.23N mentioned as that particular third order lever system would have a mechanical advantage of less than 1 whereas the mechanical advantage of the assistive device of the present invention is clearly greater than 1.

It should be understood that the assistive device of this invention can be used in combination with any simple standard inhaler and is not limited in its application to any one particular type provided that it has the adjustable leg and foot arrangement. In addition to that, the cross-sectional size of the passage through the body may be adjustable to accommodate different diameters of inhalers. This can most easily be achieved by forming a part of the body into a separate or integral strap that can be adjusted to adjust the cross-sectional size of the passage. Accordingly, a single assistive device according to the invention can be used many times in combination with many different standard inhalers.

It should be noted that the size of the body can be selected so that it can be comfortably held by a user and this may entail making it a little larger than the diameter of the inhaler in combination with which it is to be used.

It should also be noted that the invention is not limited to the provision of two levers and it is envisaged that, at least in the case of application to geriatrics, a three lever arrangement may be employed that lends itself to being gripped with a larger hand in order to move the levers towards each other in order to deliver a dose.

The assistive device of the invention also lends itself to use using additional fingers and that increases a patient's strength and thereby makes it easier to activate the inhaler with the assistive device attached. It does not "force" a child to use lateral force but rather gives the child the ability to do so. This means that the assistive device not only reduces the amount of force needed to deliver a dose, but allows for a patient to use additional fingers in which instance the assistive device is even more easily activated.

Whilst both of the two levers in the embodiment described above are movable about their proximal living hinge ends (22), it is envisaged that the principles of the invention would also be accomplished if one lever were fixed relative to the body and only the other one were movable thereby rendering the levers movable towards and away from each other as envisaged above. It may be that this variation of the invention would not be quite as effective as that described above. The relatively fixed lever would function as a lever although it does not have a specific fulcrum of its own.

In so far as the lever arrangement is concerned, it will be understood that the principles of this invention can be applied to an inhaler that is not of the metered dose type whilst the dose counter would most appropriately be applied only to metered dose types of inhalers.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. An assistive device for an inhaler wherein the assistive device comprises:
    a body defining a passage configured to receive a conventional inhaler assembly, the conventional inhaler assembly including a canister and transverse mouthpiece with an axis of the canister of the inhaler assembly approximately aligning with an axis of the passage through the body of the assistive device,
    a foot associated with the body for supporting the mouthpiece of the inhaler assembly at one end of the body when such an inhaler assembly is installed therein, and
    at least two symmetrically arranged levers supported by the body adjacent the passage and extending in a direction away from the foot and generally parallel to an axis of the body with a proximal end of each of the levers being attached to the body by an attachment that enables a free opposite end of at least one of the levers to be moved towards and away from the other, and
    an inwardly directed cam surface on each of the levers that is configured to engage a closed end of a canister of the conventional inhaler assembly when it is installed in the assistive device to move the canister longitudinally towards the foot and cause medicament to be dispensed from the canister.

2. An assistive device as claimed in claim 1 in which the foot is carried by a leg extending from the body.

3. An assistive device as claimed in claim 2 in which the length of the leg is telescopically adjustable to accommodate different lengths of conventional inhaler assemblies.

4. An assistive device as claimed in claim 3 in which the leg has a series of formations along a part of its length that may be selectively engaged by a releasable locking member that in its operative position is axially stationary relative to the body in order to set the position of the foot relative to the body.

5. An assistive device as claimed in claim 1 in which there are either two or three levers symmetrically arranged relative to the passage with the cam surfaces thereof projecting into a line of the passage so as to cooperate with corners of a closed end of the canister of the conventional inhaler when it is installed in the assistive device with its closed end located on the outside of the body on a side thereof opposite the foot.

6. An assistive device as claimed claim 1 in which the cam surfaces are curved inwardly and are designed to achieve a suitable longitudinal movement of a canister during movement of the levers towards each other so that medication is delivered by appropriate operation of the levers.

7. An assistive device as claimed in claim 1 in which the cross-sectional size of the passage through the body is adjustable to accommodate different diameters of inhalers.

8. An assistive device as claimed in claim 1 in which the assistive device is especially configured for use with a metered dose inhaler and the body of the assistive device has a support on one side thereof that supports a toothed gear dose counting mechanism having the axes of the gears extending at generally right angles to the axis of the passage with one of the toothed gears co-operating with a pawl carried on one end of a transverse arm that has its other end pivotally attached to one of the levers so that it moves transversely relative to the axis of the passage in a reciprocal manner as at least one of the levers is moved towards and away from the other.

9. An assistive device as claimed in claim 8 in which a pawl driven gear has radially shorter teeth interposed between radially longer teeth such that only the longer teeth transfer any movement to gears driven by the pawl driven gear.

10. An assistive device as claimed in claim 8 in which the toothed gear mechanism includes a pawl driven gear, a transfer gear, and a display gear carrying numerals that are visible through a suitable aperture to indicate doses remaining or doses already delivered.

11. An assistive device as claimed in claim 1 in which the at least two symmetrically arranged levers are in an arrangement complying with a second order lever system in which the mechanical advantage is greater than 1.

12. An assistive device as claimed in claim 11 in which lengths of the levers are selected according to the mechanical advantage to be achieved.

13. An assistive device as claimed in claim 1 in which the at least two symmetrically arranged levers are attached to an end of the body opposite to the end of the body having the foot and extend in a direction away from the body.

14. An assistive device as claimed in claim 1 in which the body is configured to receive the canister only between the cam surfaces and not between the at least two symmetrically arranged levers.

\* \* \* \* \*